United States Patent [19]

Tinti et al.

[11] Patent Number: 4,806,282

[45] Date of Patent: Feb. 21, 1989

[54] PROCESS FOR PREPARING GAMMA-BUTYROBETAINE

[75] Inventors: Maria O. Tinti; Domenico Misiti, both of Rome, Italy

[73] Assignee: Sigma-Tau Industrie Farmaceutiche Riunite S.p.A., Rome, Italy

[21] Appl. No.: 106,057

[22] Filed: Oct. 7, 1987

Related U.S. Application Data

[63] Continuation-in-part of Ser. No. 040,498, Apr. 25, 1987, abandoned.

[30] Foreign Application Priority Data

Apr. 24, 1986 [IT] Italy .................. 47929 A/86

[51] Int. Cl.$^4$ ................................. C07C 101/02
[52] U.S. Cl. .................... 260/501.13; 260/501.15
[58] Field of Search ............. 260/501.13, 501.15; 562/574

[56] References Cited

U.S. PATENT DOCUMENTS 4,382,092   5/1983   Carazza .................. 514/556

FOREIGN PATENT DOCUMENTS 61-65851   4/1986   Japan .................. 260/501.13

Primary Examiner—Bruce D. Gray
Attorney, Agent, or Firm—Ladas & Parry

[57]        ABSTRACT

Gamma-butyrobetaine is prepared via a process whose characterizing step comprises hydrogenating crotonoylbetaine chloride to gamma-butyrobetaine chloride is a strongly acidic environment (pH 1-4), at 15-60 psi (1.05-4.21 kg/cm$^2$) in the presence of 10% Pd/C or PtO$_2$ as hydrogenation catalyst.

3 Claims, No Drawings

PROCESS FOR PREPARING GAMMA-BUTYROBETAINE

This is a continuation-in-part of copending application(s) Ser. No. 040,498 filed on Apr. 20, 1987, abandoned.

The present invention relates to a process for preparing gamma-butyrobetaine.

Gamma-butyrobetaine, $(CH_3)_3N^+—CH_2—CH_2—CH_2COO^-$, is a natural substance. Recently it has been definitely ascertained that gamma-butyrobetaine is the immediate precursor of L-carnitine in the biosynthetic pathway of the latter compound: in fact, Gamma-butyrobetaine is hydroxylated into L-carnitine in the liver and kidneys in the presence of a specific hydroxylase enzyme.

More recently, a therapeutical use of gamma-butyrobetaine has been disclosed in the U.S. Pat. No. 4,382,092.

This patent discloses that gamma-butyrobetaine, of which no previous therapeutical utilizations were known, can be advantageously administered to patients exhibiting L-carnitine deficiency syndromes because, surprisingly, the L-carnitine deficiency is brought about by a defective biosynthesis in skeletal muscles and myocardium of gamma-butyrobetaine, and not by the defective biosynthesis of 6-N-trimethyl lysine and trimethyl 3-hydroxy-lysine, compounds which form from lysine in the previous biosynthesis steps.

At present, gamma-butyrobetaine can be obtained from gamma-butyrobetaine iodide whose preparation is described e.g. in Biochim. et Biophys. Acta, 57,327 (1962).

The preparation method disclosed in this prior art reference comprises converting gamma-aminobutyric acid (GABA) with methyl iodide in a basic environment (NaOH, KOH) into gamma-trimethylaminobutyric acid iodide.

In order to carry out GABA exhaustive methylation an excess amount (up to 3 times the stoichiometrical amount) of methyl iodide must be used and the reaction has to be carried on for 2 days. Gamma-butyrobetaine iodide is converted into the corresponding chloride or into gamma-butyrobetaine by means of ion exchange resins.

This method presents considerable drawbacks, particularly when applied on an industrial scale. The most serious drawback originates from the use of the highly toxic reagent methyl iodide. Since iodide ion is not a pharmacologically acceptable ion, having regard to the therapeutical utilization of gamma-butyrobetaine an accurate removal of both the iodide ion bonded to gamma-butyrobetaine and the inorganic iodides (NaI or KI) is mandatory. Removal of iodide ions requires a cumbersome and expensive purification step via ion exchange resins to be carried out.

Moreover, the excess of methyl iodide brings about the formation of the side-product methyl ester of gamma-butyrobetaine. In order to convert it to gamma-butyrobetaine a further hydrolysis step carried out in an acidic environment is required.

The process for preparing gamma-butyrobetaine according to the present invention is illustrated in the following reaction scheme:

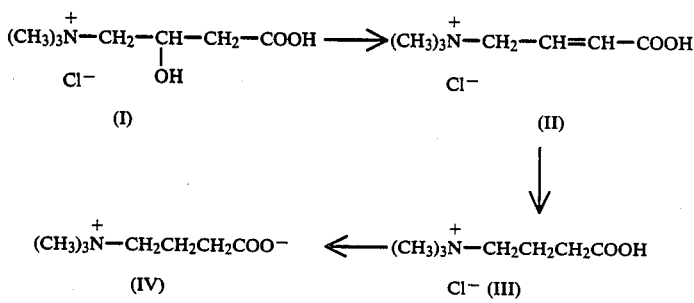

and comprises:

(a) converting D-carnitine chloride (I) into crotonoylbetaine chloride (II) via known procedures;

(b) converting crotonoylbetaine chloride (II) into gamma-butyrobetaine chloride (III) by hydrogenating (II) in water or watersoluble solvent, at pH comprised between 1 and 4, at hydrogen pressure comprised between 15 and 60 psi (1.05–4.21 kg/cm2), at 10° to 50° C. in the presence of a hydrogenation catalyst; and (c) converting (III) into (IV) by means of a strongly basic ion exchange resin activated in the OH$^-$ form via known procedures.

Step (a), conversion of D-carnitine chloride (I) into crotonylbetaine chloride is detailed in "The Resolution of ±Carnitine and the Synthesis of Acylcarnitines" Brendel and Bressler, BBA 98; 104. The conversion occurs by heating d-carnitine chloride (I) under reflux in a 1:1 (w/v) mixture of acetic acid and acetic anhydride for 10 mins. A 90% yield is obtained after the acetic acid and acetic anhydride were removed by evaporation in vacuo. The crotonylbetaine chloride may be recrystallized from isopropanol, and has a melting point of 205° C.

Step (c), the conversion of a chloride to the inner sale is described by E. Strack in "Darstelling von O-acyl-carnitinen, Hoppe-Seyler's Z. Physiol. Chem. 351:95-98 Jan. 1970.

Preferably, the hydrogenation catalyst is either 10% Pd/C, or PtO$_2$ and the watersoluble solvent is selected from methanol and ethanol.

The featuring step of the process of the present invention is the hydrogenation step which must be carried out strictly following the above-specified operating conditions, particularly with regard to the strongly acidic pH (1 to 4) of the reaction phase. In fact, it has been found that, and pH increases, hydrogenation of crotonoylbetaine chloride leads to formation of reaction products other than the desired product. Furthermore, it should be regarded as surprising that the hydrogenation reaction takes place at a more than satisfying reaction rate because it is known (see e.g. "Catalytic Hydrogenation" by Robert L. Augustine, page 46, Marcel Dekker, Inc. (1965)) that the hydrogenation rate of the double bond in alfa-beta unsaturated carbonyl compounds is decreased if hydrogenation takes place in an acidic environment.

The process of the present invention presents remarkable advantages over the known method. Above all, methyl iodide the use of which entails the serious drawbacks which have been outlined above, is no longer needed. A further advantage of the process of the present invention is that, in place of the costly gamma-aminobutyric acid, D-carnitine is used as starting material. D-carnitine is obtained as side-product in the preparation of L-carnitine via resolution of either D,L-carnitine or D,L-carnitinamide racemic mixtures. To date, no previous utilizations of D-carnitine have been known.

The non-limiting example that follows illustrates the preparation of gamma-butyrobetaine in accordance with the present invention.

EXAMPLE (a) Preparation of gamma-butyrobetaine chloride

To a solution of crotonoylbetaine chloride (1.8 g; 0.01 moles) in 20 cc of $H_2O$, 5% HCl was added until pH 2 was reached. 450 mg of 10% Pd/C* were added to the solution and the resulting reaction mixture was hydrogenated in a Parr hydrogenator under pressure (50 psi; 3.51 kg/cm2) at room temperature.

*10% by weight of palladium on the overall mixture of palladium charcoal (see Seki, Chem. Pharm. Bull. 20:362 (1972))

After 2 hours the hydrogenation was complete. The aqueous solution was concentrated to dryness under vacuum, the solid residue was washed with acetone. Gamma-butyrobetaine chloride was obtained as a pure solid product (yield: about 80%) M.P. 208°–210° C.

| HPLC | Waters |
|---|---|
| Pressure | 800 psi (56.25 kg/cm$^2$) |
| Column | μ Bondapak NH$_2$ |
| Eluent | KH$_2$PO$_4$ 0.05 M—CH$_3$CN 35-65 |
| Flow rate | 1 ml/min |
| Detector | U.V.λ205 |
| Chart speed | 0.5 cm/min |
| Rt | 12.47 (corresponding to Gamma-butyrobetaine prepared via the known method) |
| Crotonoyl betaine chloride | absent (Rt = 11.5) |
| TLC | |
| Chloroform, methanol, isopropanol, H$_2$O, acetic acid | |
| 6           4           1           1.5   1.5 | |
| R$_f$ = 0.3 | |

NMR D$_2$O δ 3.5(2H, d, N$^+$—CH$_2$—): 3.2 (9H, s,(CH$_3$)$_3$d, —CH$_2$COOH): 2.3 (2H, m, CH$_2$—CH$_2$-CH$_2$).

(b) Conversion of gamma-butyrobetaine chloride to gamma-butyrobetaine.

Gamma-butyrobetaine (1 g) was dissolved in water and the resulting solution was fed at the top of a column containing 10 grams of AMBERLITE IRA 402 resin activated in the OH$^-$ form. The resin was eluted with water and the fractions at pH 7 containing gamma-butyrobetaine inner salt were collected under TLC control conditions. The pooled fractions were lyophilized and a white pure solid product (0.8 g) was obtained. M.P. =253° C.

NMR and HPLC as for gamma-butyrobetaine chloride.

Elementary analysis: corresponding to C$_7$H$_{15}$NO$_2$.
Chlorine: absent

What is claimed is:

1. A process for preparing gamma-butyrobetaine according to the following reaction scheme:

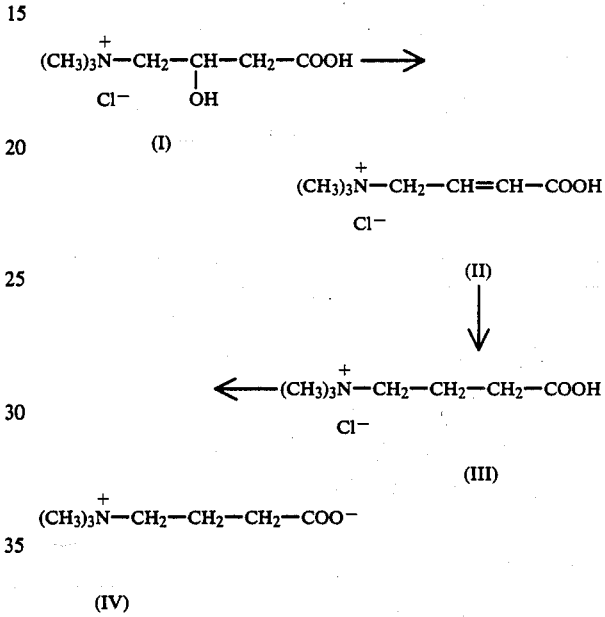

which comprises
(a) converting D-carnitine chloride (I) into crotonoylbetaine chloride (II);
(b) converting crotonoylbetaine chloride (II) into gamma-butylrobetaine chloride (III) by hydrogenating (II) in water or watersoluble solvent, at pH comprised between 1 and 4, at hydrogen pressure comprised between 15 and 60 psi (1.05-4.21 kg/cm2), at 10 to 50° C. in the presence of a hydrogenation catalyst; and
(c) converting (III) into (IV) by means of a strongly basis
ion exchange resin activated in the OH$^-$ form.

2. The process of claim 1 wherein the hydrogenation catalyst is selected from 10% Pd/C, and PtO$_2$.

3. The process of claim 1, wherein the watersoluble solvent is selected from methanol and ethanol.

* * * * *